(12) United States Patent
Feldman et al.

(10) Patent No.: US 8,628,788 B2
(45) Date of Patent: Jan. 14, 2014

(54) FORMULATIONS CONTAINING A NON-OXIDATIVE BIOCIDE AND A SOURCE OF ACTIVE HALOGEN AND USE THEREOF IN WATER TREATMENT

(75) Inventors: David Feldman, Haifa (IL); Michel Adda, Kfar-Saba (IL); Raymond J. Roccon, Cranberry Township, PA (US)

(73) Assignee: Bromine Compounds, Ltd., Beer-Sheva (IL)

( * ) Notice: Subject to any disclaimer, the term of this patent is extended or adjusted under 35 U.S.C. 154(b) by 1505 days.

(21) Appl. No.: 11/922,952

(22) PCT Filed: Feb. 25, 2007

(86) PCT No.: PCT/IL2007/000245
§ 371 (c)(1),
(2), (4) Date: Dec. 27, 2007

(87) PCT Pub. No.: WO2007/096885
PCT Pub. Date: Aug. 30, 2007

(65) Prior Publication Data
US 2009/0117202 A1 May 7, 2009

Related U.S. Application Data

(60) Provisional application No. 60/776,419, filed on Feb. 24, 2006.

(51) Int. Cl.
*A01N 37/18* (2006.01)
*A01N 59/02* (2006.01)
*A01N 59/00* (2006.01)
*A01P 1/00* (2006.01)
*A61K 31/275* (2006.01)
*A61K 33/14* (2006.01)
*A61K 33/20* (2006.01)
*A61K 33/40* (2006.01)

(52) U.S. Cl.
USPC ........... 424/405; 424/613; 424/661; 424/722; 424/723; 514/389; 514/515; 514/626

(58) Field of Classification Search
None
See application file for complete search history.

(56) References Cited

U.S. PATENT DOCUMENTS

| | | | |
|---|---|---|---|
| 3,689,660 A | 9/1972 | Burk et al. | |
| 3,928,575 A | 12/1975 | Moyle et al. | |
| 4,163,795 A | 8/1979 | Burk | |
| 4,163,796 A | 8/1979 | Burk | |
| 4,163,797 A | 8/1979 | Burk | |
| 4,232,041 A | 11/1980 | Burk et al. | |
| 4,328,171 A * | 5/1982 | Burk et al. | 514/526 |
| 4,604,405 A | 8/1986 | Jakubowski | |
| 4,879,306 A * | 11/1989 | Henkels et al. | 514/441 |
| 5,627,135 A * | 5/1997 | Gartner | 504/159 |
| 6,083,890 A | 7/2000 | Miskiel et al. | |
| 2002/0147235 A1 | 10/2002 | Carlson et al. | |
| 2006/0003023 A1 | 1/2006 | Williams | |
| 2007/0160676 A1 | 7/2007 | Pendse et al. | |
| 2009/0117202 A1 | 5/2009 | Feldman et al. | |

FOREIGN PATENT DOCUMENTS

| | | |
|---|---|---|
| DE | 2854078 A1 | 6/1979 |
| EP | 954966 B1 | 6/2003 |
| EP | 1322600 B1 | 3/2004 |
| IL | 0065290 | 3/1982 |
| JP | 09295907 | 11/1997 |
| WO | WO98/25458 | 6/1998 |

OTHER PUBLICATIONS

Exner et al., "Rates and Products of Decomposition of 2,2-dibromo-3-nitrilopropionamide", J. Agr. Food Chem., vol. 21, No. 5, pp. 838-842, 1973.

* cited by examiner

*Primary Examiner* — Ernst Arnold
(74) *Attorney, Agent, or Firm* — Dilworth & Barrese, LLP

(57) ABSTRACT

Novel formulations containing a non-oxidative biocide, such as DBNPA, and a source of an in situ produced active biocide, such as a concentrated aqueous solution of an inorganic halide salt, are disclosed. These novel formulations are particularly effective in the treatment of water, and are characterized by high stability, desirable rheological properties and an excellent biocidal activity.

19 Claims, 1 Drawing Sheet

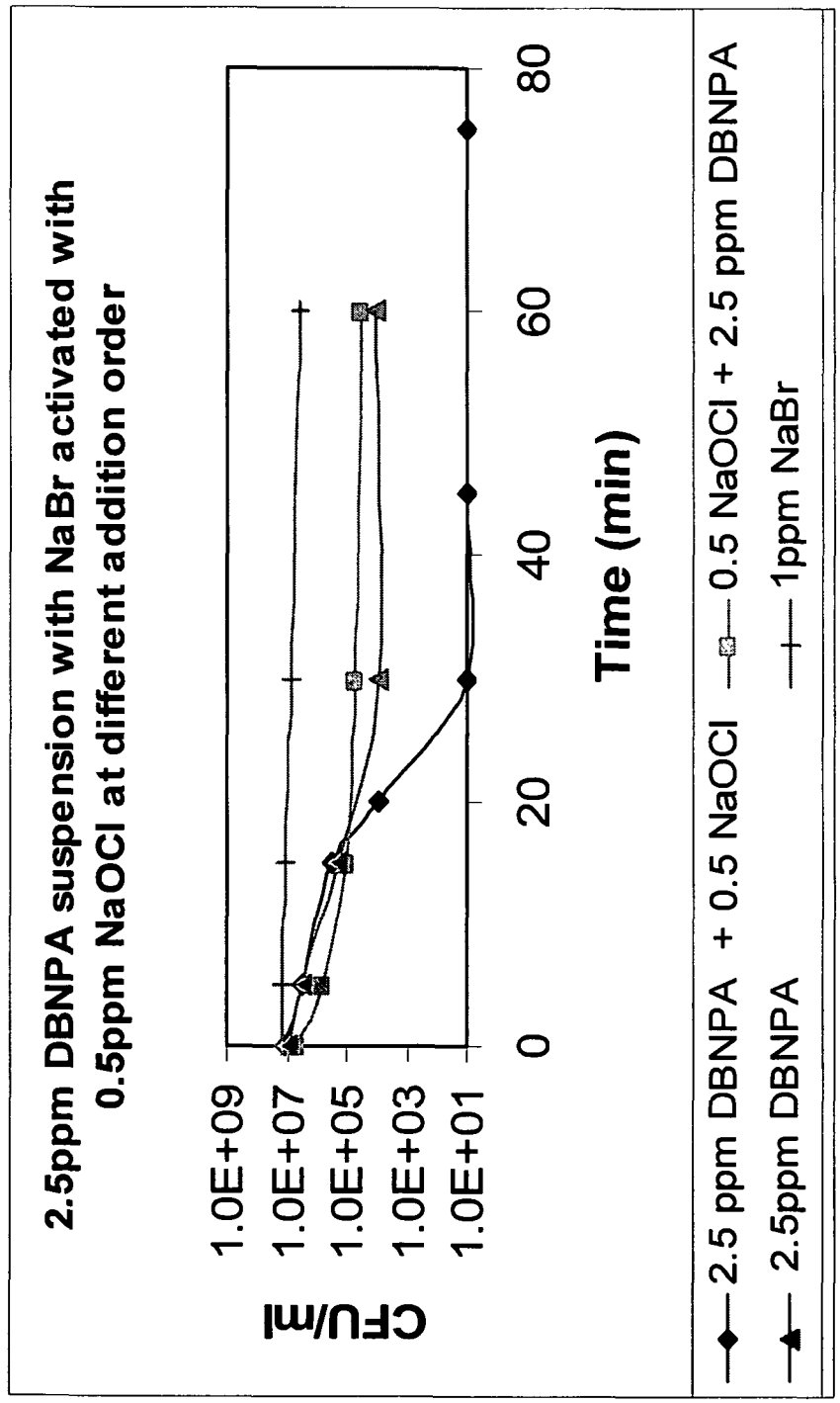

FORMULATIONS CONTAINING A NON-OXIDATIVE BIOCIDE AND A SOURCE OF ACTIVE HALOGEN AND USE THEREOF IN WATER TREATMENT

RELATED APPLICATIONS

This application is a National Phase of PCT Patent Application No. PCT/IL2007/000245 having International Filing Date of Feb. 25, 2007, which claims the benefit of U.S. Provisional Patent Application No. 60/776,419 filed on Feb. 24, 2006. The contents of the above applications are all incorporated herein by reference.

BACKGROUND OF THE INVENTION

The present invention relates to the field of water purification and, more particularly, to novel formulations for water disinfestation, containing a combination of a non-oxidative biocide and a source of an oxidative biocide.

Biocidal treatment is an essential part of any water treatment, in particular when treating industrial water, and is used to prevent microbiological growth, biocorrosion and biofouling accumulation. Biocides are often classified according to their mode of operation, with the most common classification being between oxidative and non-oxidative biocides. Oxidative and non-oxidative biocides are commonly combined in order to increase the biocidal efficiency of the treatment program.

Commonly used oxidative biocidal agents include active halogen-releasing compound such as chlorine, bromine, hypochlorous acids and hypochlorite salts thereof, and hypobromous acids and hypobromite salts thereof, as well as chlorine or bromine carriers such as halogenated hydantoins and halogenated isocyanurates.

"Active halogen" is a phrase used herein to describe halogen compounds or species in which the halogen atom has a +1 oxidation state (for example ClO$^-$ and BrO$^-$), and is also known and referred to in the art as "free halogen" or "available halogen". Active halogens are known as highly effective antimicrobial agents, having a wide biocidal activity (e.g., antibacterial, antifungal, antialgae and antiviral activities), and thus are routinely used in water treatment systems.

Hypochlorous and hypobromous acids (HOCl and HOBr respectively) are common sources of active halogen and are frequently used as aggressive oxidizing agents for various applications, including water treatment systems.

In water, the active halogen ion exists in equilibrium with the corresponding acid, which in turn is in equilibrium with dissolved halogen gas (see, scheme 1 below), whereby the relative proportions of the active halogen and the corresponding acid are determined by pH and temperature.

Scheme 1

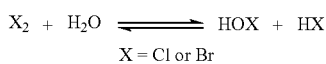

X = Cl or Br

For example, in a chlorine based system, when the pH is between 2 and 7, the equilibrium is in favor of HOCl. As the pH falls below 2, the predominant form of the chlorine is Cl$_2$. At a pH of 7.4, HOCl and OCl$^-$ are about equal, and as the pH goes above 7.4, increasing proportions of OCl$^-$ are present.

The hypochlorite and hypobromite ions are less effective oxidizing agents than the corresponding acids.

Chlorine based oxidants, such as hypochlorous acid, have several limitations, as compared to bromine based oxidants. First, at a pH higher than 7.5 (an industrially-common pH of, for example, cooling water) the main species is the hypochlorite ion (OCl$^-$), and not the more active biocidal species, hypochlorous acid (HOCl). Furthermore, hypochlorous acid reacts irreversibly with amines to produce chloroamine, which is also less active as biocide.

Hypobromous acid is a more efficient biocide compared to hypochlorous acid for the following reasons: (i) at a pH of about 8-9, the amount of non-dissociated hypobromous acid is higher than that of non-dissociated hypochlorous acid; (ii) the reaction of hypobromous acid with amines is reversible and thus, the presence of amines does not affect the efficiency of the biocide; and (iii) at the same pH and temperature, the volatility of the hypobromous acid is lower than that of the hypochlorous acid, therefore loss by evaporation is reduced.

Hypobromous acid is obtained by reacting sodium bromide with chlorine-based oxidants. The hypobromous acid then reacts with the reactive species (inorganic, organic or microbes) and bromide (Br$^-$) is regenerated into the water.

Thus, commonly used water treatment systems often utilize sodium bromide (usually as a concentrated (e.g., 40%) aqueous solution thereof, otherwise known as "brine") in combination with an oxidant such as hypochlorite, so as to generate the active hypobromous acid, as depicted in scheme 2 below:

Scheme 2

As discussed hereinabove, non-oxidative biocidal agents are also frequently used in water purification systems. These include, for example, aldehydes (e.g., formaldehyde, glutaraldehyde and acrolein), amine-type compounds (e.g., quaternary ammonium compounds), halogenated compounds (e.g., bronopol (2-bromo-2-nitro-1,3-propanediol)), terbutylazine (TBZ), 1,2-dibromo-2,4-dicyanobutane (DBDCB), 2,2-dibromo-3-nitrilopropionamide (DBNPA)), sulfur-containing compounds (e.g., isothiazolone, thiocarbamates, thiocyanomethylbenzothiazole, copper sulfate and metronidazole), and quaternary phosphonium salts (e.g., tetrakis (hydroxymethyl)phosphonium sulfate (THPS)).

2,2-Dibromo-3-nitrilopropionamide, referred to hereinafter interchangeably as DBNPA (presented in Scheme 3 below), is a broad range non-oxidative haloacetamide biocide, commonly used for disinfection of cooling water and industrial water treatment. The solubility of DBNPA in water, at ambient temperature, is only 1.7%. DBNPA is also highly unstable in water, as it quickly degrades into ammonia and a bromide ion. DBNPA is more stable under acidic aqueous conditions, typically in a pH range of 1 to 5 [see, for example, "Rates and Products of Decomposition of 2,2-dibromo-3-nitrilopropionamide", Exner et al., *J. Agr. Food Chem.*, Vol. 21, No. 5, pp. 838-842, 1973].

Scheme 3

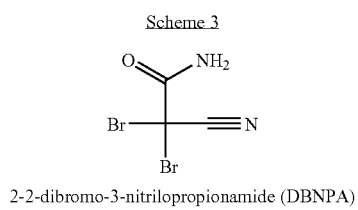

2-2-dibromo-3-nitrilopropionamide (DBNPA)

Haloacetamides in general, and DBNPA in particular, can be utilized in water treatment systems via various modes of applications.

The most common mode of application of DBNPA is as a liquid formulation. Since DBNPA has poor solubility in water, these formulations typically contain as a carrier a mixture of water and an organic solvent, most often a glycol (for example, polyethylene glycol (PEG), dipropylene glycol (DPG) and others). Although the concentration of the DBNPA in such liquid formulations may reach 50%, usually, it is reported as being from 5% to 25%, with a concentration of glycol of at least 45% glycol.

The use of organic solvents, however, is generally undesirable due to cost ineffectiveness and environmental concerns, mainly due to an increase of the organic loading of the treated water (chemical oxygen demand, COD) (see, for example, U.S. Pat. No. 5,627,135).

Liquid formulations of DBNPA, combining organic solvents and water, are described, for example, in U.S. Pat. No. 4,163,796, which teaches aqueous antimicrobial compositions containing 2.5% DBNPA; in U.S. Pat. Nos. 4,163,797 and 4,232,041 and DE 2,854,078, which teach aqueous antimicrobial compositions containing 5% DBNPA; in U.S. Pat. No. 4,163,795, which teaches aqueous antimicrobial compositions containing 10% DBNPA; and in U.S. Pat. No. 3,689,660, which teaches stable liquid compositions useful as antimicrobial agents, containing 15-25% DBNPA. In IL Patent No. 0065290, by the present assignee, aqueous antimicrobial compositions containing 10% DBNPA are disclosed.

DBNPA sustained-release formulations are also common, containing various additives, such as polymeric matrices (for example, methyl cellulose), binders and compression agents in a significant amount. Exemplary sustained-release formulations are described in European Patent No. 954966 and in WO 98/25458. Sustained-release formulations have similar drawbacks as the soluble liquid formulation, as such formulations contain inert components that lead to an increase of the cost and the organic loading. In addition, in most of these formulations the rate of the DBNPA dissolution is not constant, thus preventing optimal control of the water body.

Alternatively, DBNPA is formulated as solid compacted products, available as granules or tablets (see, for example, European Patent No. 1322600). This mode of application is direct and circumvents using a solvent. However, it requires a suitable feeding system which may complicate the application.

In order to overcome the disadvantageous features of the above-described formulations, aqueous suspensions of DBNPA can be utilized. Such suspensions are typically obtained with the aid of suspending agents. Since DBNPA is stable in water only under acidic environment, special suspending agents, which are stable at a pH below 5, are required. Unfortunately, most of the commonly used suspending agents are either unstable or fail to exhibit the desired effect under acidic conditions.

For example, U.S. Pat. No. 5,627,135 teaches aqueous suspensions of DBNPA having a pH in the range of 1 to 4 and containing xanthan gum as a proposed thixotropic suspending agent. The suspending agent is defined therein as "a thixotrope that exhibits Ellis-Plastic behavior", which suggests a high viscosity for avoiding sedimentation in a static state, and a moderate viscosity when pumping the slurry. The suspensions taught in this patent comprise DBNPA at a concentration range of from 3% to 70% by weight in water.

Japanese patent No. 09295907 discloses a suspension of DBNPA in water with rhamsan gum as a suspending agent, and no reference to pH control.

U.S. Pat. No. 6,083,890 teaches that in DBNPA-containing compositions stored for 7 days at ambient temperature and a pH of about 2.2 or less, xanthan gum loses a significant proportion, greater than 20%, of its viscosifying functionality. Such a functionality loss evidently leads to poor product performance unless an increased concentration of xanthan gum is initially used to compensate for the decrease in viscosity. Thus, the desirability of a low pH to preserve the haloacetamide conflicts with the adverse effects of a low pH on a suspending agent such as natural xanthan gum.

U.S. patent application Ser. No. 10/052,115 having publication No. 20020147235 discloses suspensions of haloacetamides in which a special group of xanthan gums which contain no more than 1.2% acetic acid or acetate groups by weight, is utilized. This particular xanthan gum group is more stable than the common xanthan gums.

Several reports teach using DBNPA in combination with other non-oxidative biocides. For example, since DBNPA is active against some types of algae only at high concentrations, it has been utilized in combination with highly active anti-algae agents, such as terbutylazine (TBZ), mostly in aqueous suspensions, or 1,2-dibromo-2,4-dicyanobutane (dibromodicyanobutane, DBDCB) (see, for example, U.S. Pat. No. 4,604,405).

As discussed hereinabove, oxidative and non-oxidative biocides are commonly combined in order to increase the biocidal effect in water treatment. Thus, several publications describe formulations that combine a non-oxidative agent such as DBNPA and an agent capable of forming an oxidizing agent, such as sodium bromide.

Thus, for example, liquid formulations containing 5% or 20% DBNPA, as well as NaBr, HBr, hypobromous acid, water and tetraethylene glycol, which are used for disinfecting pulp and paper, and solid slow-released DBNPA solid tablets have been described (see, http://www.amsainc.com/prod-dbnpa-overview.asp).

DBNPA liquid solutions in polyethylene glycol (PEG) 200 and/or tetraethyleneglycol and water (for example a 5% or 20% DBNPA formulation) are also disclosed (see, www-.dowbiocides.com).

U.S. Pat. No. 3,928,575 discloses a solid composition of a halocyanoacetamide, such as DBNPA, and at least 0.5 mole of a water-soluble bromide or iodide salt (such as sodium iodide), typically below 10 moles, per mole of halocyanoacetamide, which was found effective in rapid destruction of microorganisms. This patent suggests that the antimicrobial activity of such a composition results from potentiation of the halocyanoacetamide by the halide salt and that such a potentiation results in synergism. The solid compositions taught in this patent, however, typically includes from 1 to 10 weight percents of the halocyanoacetamide. No reference is made in this patent to a combination of DBNPA with an oxidative biocide, nor to an activation of the bromide or iodide salt, so as to produce an oxidative biocide.

Although these publications describe soluble liquid formulations or solid formulations that contain combinations of DBNPA and bromides, these formulations suffer many disadvantages, such as limited concentration of DBNPA, high cost and non-friendly reagents, as discussed in detailed hereinabove. Currently known aqueous suspensions of DBNPA also suffer disadvantages such as instability, limited concentration of DBNPA and/or insufficient efficacy.

Thus, there is a widely recognized need for, and it would be highly advantageous to have, novel, stable formulations that contain a combination of oxidative and non-oxidative reagents, which can be beneficially used in water disinfestation, and are devoid of the above limitations.

SUMMARY OF THE INVENTION

The present invention provides novel formulations that comprise a non-oxidative biocide and an in situ produced active halogen source, preferably generated from an inorganic halide salt. These formulations were found to be highly stable, as aqueous suspensions or as liquid formulations, even when high concentrations of the biocide are used. These formulations were further found highly effective in water treatment, particularly in water disinfestation.

Thus, according to one aspect of the present invention there is provided a formulation comprising at least one non-oxidative biocide and a concentrated aqueous solution of an inorganic halide salt, the formulation being in a form of a suspension.

According to further features in preferred embodiments of the invention described below, the halide salt produces an active halogen upon activation by an oxidizer.

According to still further features in the described preferred embodiments the oxidizer is selected from the group consisting of chlorine, bromine, hypochlorite salt, hypochlorous acid, hypobromite salt, hypobromous acid a halogenated hydantoin, a halogenated isocyanurate, a peroxide and a persulfate.

According to another aspect of the present invention there is provided a formulation comprising at least one non-oxidative biocide, a source of an in situ produced active halogen and an aqueous solvent, the formulation being in a form of a suspension.

According to further features in preferred embodiments of the invention described below, the active halogen is produced in situ upon activation by an oxidizer.

According to still further features in the described preferred embodiments the source of the active halogen is a concentrated aqueous solution of an inorganic halide salt.

According to yet another aspect of the present invention there is provided a formulation comprising 2,2-dibromo-3-nitrilopropionamide (DBNPA) and sodium bromide brine, the formulation being in a form of a suspension.

According to further features in preferred embodiments of the invention described below, the sodium bromide produces an active halogen upon activation by an oxidizer.

According to still further features in the described preferred embodiments the formulation further comprises at least one additional biocide.

According to still further features in the described preferred embodiments an amount of the DBNPA and the sodium bromide is greater than 30 weight percents of the total weight of the formulation.

According to still further features in the described preferred embodiments an amount of the DBNPA ranges from 3 weight percents and 70 weight percents of the total weight of the formulation. Preferably, the amount of the DBNPA is greater than 20 weight percents of the total weight of the formulation.

According to still further features in the described preferred embodiments the DBNPA and the sodium bromide and/or active halogen formed thereby act in synergy.

According to still further features in the described preferred embodiments the formulation described herein is characterized by a shear rate higher than 300 Pa at a speed smaller than 100 rpm.

According to still further features in the described preferred embodiments the formulation described herein is characterized by a shear rate lower than 300 Pa at a speed equal to or higher than 100 rpm.

According to still further features in the described preferred embodiments an average particle size of the non-oxidative biocide or the DBNPA in the suspension is less than 200 microns.

According to still further features in the described preferred embodiments there is provided the formulation described herein, further comprising a suspending agent. Preferably, an amount of the suspending agent is lower than 2 weight percents of the total weight of the formulation. Yet preferably, the suspending agent is a water-soluble suspending agent.

According to still further features in the described preferred embodiments there is provided the formulation described herein, further comprising a foaming agent.

According to still another aspect of the present invention there is provided a liquid formulation comprising at least one non-oxidative biocide, a concentrated aqueous solution of an inorganic halide salt, and a polyethylene glycol having an average molecular weight higher than 100 grams/mol.

According to further features in preferred embodiments of the invention described below, an amount of the polyalkylene glyocol is lower than 50 weight percents of the total weight of the formulation.

According to still further features in the described preferred embodiments, the amount of the non-oxidative biocide and the halide salt is greater than 70 weight percents of the total weight of the formulation.

According to still further features in the described preferred embodiments there is provided the formulation described herein, wherein an amount of the non-oxidative biocide ranges from about 3 weight percents to about 70 weight percents of the total weight of the formulation.

According to still further features in the described preferred embodiments t the amount of the non-oxidative biocide is greater than 50 weight percents of the total weight of the formulation.

According to still further features in the described preferred embodiments the at least one non-oxidative biocide is selected from the group consisting of an aldehyde-based non-oxidative biocide, an amine-containing non-oxidative biocide, an amide-containing non-oxidative biocide, an imide-containing non-oxidative biocide, a halogenated non-oxidative biocide, a sulfur-containing non-oxidative biocide, a quaternary phosphonium-containing non-oxidative biocide, an ammonium salt-containing non-oxidative biocide and any combination thereof. Preferably, the halogenated non-oxidative biocide is selected from the group consisting of bronopol, terbutylazine, 1,2-dibromo-2, 4-dicyanobutane, 2-bromo-2-cyano-acetamide, 2,2-dibromo-2-cyanoacetamide, 2-bromo-2-chloro-2-cyanoacetamide and 2,2-dibromo-3-nitrilopropionamide.

According to still further features in the described preferred embodiments the at least one non-oxidative biocide comprises 2,2-dibromo-3-nitrilopropionamide (DBNPA).

According to still further features in the described preferred embodiments the concentrated aqueous solution of the inorganic halide salt is a saturated solution of the halide salt.

According to still further features in the described preferred embodiments the inorganic halide salt is selected from the group consisting of an inorganic bromide salt and an inorganic chloride salt.

According to still further features in the described preferred embodiments the inorganic halide salt is an inorganic bromide salt. Preferably, the inorganic bromide salt is selected from the group consisting of sodium bromide, magnesium bromide, calcium bromide, lithium bromide, ammonium bromide and potassium bromide.

According to still further features in the described preferred embodiments, in each of the formulations described herein, the at least one non-oxidative biocide and the inorganic halide salt and/or active halogen formed thereby act in synergy.

According to still further features in the described preferred embodiments each of the formulations described herein is stable for at least 1 week upon storage at ambient temperature. Preferably, the formulation is stable for at least 10 days upon storage at ambient temperature.

According to still further features in the described preferred embodiments each of the formulations described herein is stable for at least 1 week upon storage at 50° C.

According to still further features in the described preferred embodiments the formulations described herein are identified for use in water disinfection.

According to an additional aspect of the present invention there is provided a method of water disinfestation, the method comprising contacting the water with at least one non-oxidative biocide and an in situ-produced active halogen.

According to further features in preferred embodiments of the invention described below, the active halogen is obtained by an in situ activation of an inorganic halide salt by an oxidizer.

According to still further features in the described preferred embodiments the at least one non-oxidative biocide is 2,2-dibromo-3-nitrilopropionamide (DBNPA).

According to yet an additional aspect of the present invention there is provided a method of water disinfestation, the method comprising contacting the water with any of the formulations as described herein.

According to further features in preferred embodiments of the invention described below, the contacting is performed intermittently.

According to still further features in preferred embodiments of the invention described below, the contacting is performed continuously.

According to still further features in the described preferred embodiments the method further comprising contacting the water with an oxidizer.

The present invention successfully addresses the shortcomings of the presently known configurations by providing novel formulations, which exhibit exceptional stability, biocidal efficacy and rheological behavior, and are thus far superior to known biocidal formulations.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 presents comparative plots demonstrating the synergistic effect of a DBNPA/NaBr aqueous suspension containing 58 weight percents DBNPA, upon incubation with bacterial beads in the presence of sodium hypochlorite.

DESCRIPTION OF THE PREFERRED EMBODIMENTS

The present invention is of novel formulations containing a combination of a non-oxidative biocide and an in situ produced active halogen as an oxidative biocide, which can be advantageously utilized for water disinfestation. Specifically, the present invention is of aqueous suspensions of a non-oxidative biocide and a source of an in situ produced oxidative biocide, preferably being a concentrated aqueous solution of an inorganic halide salt, which are highly stable, and exhibit desirable rheological properties, when a high concentration of the biocide is utilized, and further exhibit a high biocidal activity. The present invention is further of liquid formulations containing a non-oxidative biocide and a source of an in situ produced oxidative biocide, preferably being an inorganic halide salt and an organic solvent. The present invention is further of processes of preparing these formulations and of methods utilizing same, preferably in combination with an oxidizer, for treating contaminated water.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As discussed in detail hereinabove, biocidal treatment of water (also known as water disinfestation) involves oxidative and non-oxidative biocides.

Active halogens are known as highly effective oxidative antimicrobial agents, having a wide biocidal activity, and are indeed frequently used in water treatment systems. Among active halogens, bromine-based oxidative biocides are considered superior to chlorine-based oxidative biocides for many industrial water treatment applications. Active bromines are obtained, for example, by reacting sodium bromide, either solid or in aqueous/brine solutions, with chlorine-based oxidants.

Amongst the commonly used non-oxidative biocides, halogenated compounds, such as bronopol, terbutylazine (TBZ), 1,2-dibromo-2,4-dicyanobutane (dibromodicyanobutane, DBDCB) and 2-2-dibromo-3-nitrilopropionamide (DBNPA), constitute an important group.

As further discussed in detail hereinabove, DBNPA is a common and effective non-oxidative biocide, often used in industrial water treatment. Most of the currently known formulations of DBNPA include liquid formulations, sustained-release formulations and solid compositions. However, these formulations suffer several disadvantages, as follows:

(a) the low solubility and instability of DBNPA in water often necessitates using organic solvents, such as polyethylene glycols, in very high concentrations (up to about 60%), a feature which is environmentally and economically undesirable, and increases the organic loading of the treated water;

(b) the concentration of the DBNPA in these liquid formulations is usually low, between 5% to 25%;

(c) DBNPA sustained-release formulations have similar drawbacks as the soluble liquid formulation, and in addition, the DBNPA dissolution is not constant and controlling the water treatment process is difficult; and (d) using solid compacted DBNPA requires a suitable feeding system which may complicate its application.

Due to the environmental and economical deficiencies of liquid formulations and limited applications of solid compositions, aqueous suspensions of DBNPA and other non-oxidative biocides is an attractive form for formulating such agents. Such a formulation form is produced at much lower cost, compared to liquid formulations, and results in a much lower environmental impact (due to a decreased Carbon Oxygen Demand (COD)), while avoiding the risk of solvent-based products actually encouraging biogrowth. Further, aqueous suspension forms are favorable in comparison to solid formulations, since they are more easily controlled, and do not require a particularly suitable feeding system.

However, as discussed hereinabove, aqueous suspensions of DBNPA require the use of suspending agents, whereby most commonly-used suspending agents are unstable under acidic conditions, in which the DBNPA is stable.

Furthermore, when intended for an industrial application, aqueous suspensions should exhibit certain properties, in order to allow an efficient utilization thereof. Such an industrial suspension has to be pseudo-plastic, namely, to show a high viscosity at low shear rate, so as to avoid settling of the solid; and to show a low viscosity at higher shear rate, so as to permit flow and pumping of the suspension. The rheological behavior of the suspension is dependant on the solid particles' size, the charge distribution on the solid's surface and on the pH, the ionic strength and the viscosity of the suspending phase.

Some aqueous suspensions of DBNPA are disclosed in the art, yet, most are unsuitable for the industrial water treatment applications, due to the conflict of DBNPA stability and suspending agent stability at high pH values In a search for formulations that could be utilized in an efficacious, cost-effective and environmental-friendly method of treating water, the present inventors have now surprisingly found that non-oxidative biocides such as DBNPA can be successfully formulated with a concentrated aqueous solution of an inorganic halide salt such as sodium bromide brine. Inorganic halide salts can serve as a source of an active halogen (formed upon contacting the halide salt with an oxidizer) and hence, such formulations combine oxidative and non-oxidative biocides. The present inventors have further surprisingly found that these formulations can be formed as highly stable aqueous suspensions that are characterized by the desired rheological properties and by the desired biocidal activity for the disinfection of water.

As demonstrated in the Examples section that follows, organic solvent-free, aqueous suspension formulations, containing high concentrations of DBNPA, in combination with various halide brines, were prepared, and exhibited a high stability, desirable viscosity and high biocidal efficacy. For example, a 55% milled DBNPA aqueous suspension, containing a solution of 40% NaBr brine, was tested in a field test and was demonstrated to reduce the bacterial count in a cooling water tower from above $10^5$ CFU/ml to lower than $10^3$ CFU/ml (see, Example 22), within a few days (CFU=Colony Forming Units).

Thus, according to one aspect of the invention there is provided a formulation which comprises one or more non-oxidative biocides and a concentrated aqueous solution of an inorganic halide salt, the formulation being in a form of a suspension.

As used herein and is well known in the art, the term "suspension" describes an intimate mixture of two substances: the suspended (dispersed) phase (suspenoid), which includes a substance in a finely divided state, which is uniformly distributed through the second substance, called the suspending phase (or dispersing medium). The suspending phase may be a gas, a liquid, or a solid and the suspended phase may also be any of these, with the exception of one gas in another. A suspension typically separates itself by gravitational action into two visibly distinct portions over time. Such a phenomenon is also commonly referred to as settling out and a stability of a suspension is typically defined by the time period required for the settling out to be effected.

An "aqueous suspension" is therefore a suspension as defined herein in which the suspended phase includes solid particles and the suspending phase is an aqueous solution.

As used herein, the term "biocide" describes an agent that is capable of destroying or killing an organism, or of materially inhibiting the growth of an organism.

The term "organism" is used herein to describe organisms which are typically pathogenic to humans or animals during one or more of their life cycles, or disrupt the local ecology. This term further encompasses organisms, which, although not pathogenic or ecologically disruptive, are typically destructive of industrial processes or equipment.

Examples include fungi and their spores, protozoans and their cysts, bacteria and their spores, algae, viruses, helminthes or their ova, insects, small fish and their ova, mollusks and their ova, and other types of living organisms. The organisms may be micro-cellular, uni-cellular, multi-cellular, and the like. Preferably, the biocides utilized in the context of the present invention are suitable for use against organisms, in particular microorganisms, that typically grow in watery environments. These include, for example, bacteria, viruses, coliforms, fungi and algaes.

The term "non-oxidative biocide", also referred to herein interchangeably as "non-oxidative agent", "non-oxidizing agent" and "non-oxidizing biocide", refers to a biocide which, while during the disinfestation (interfering with the life cycle of an organism) process, does not undergo a change in its oxidation state.

Preferred non-oxidative biocides, according to the present embodiments include, but are not limited to, aldehyde-based non-oxidative biocides, amine-based non-oxidative biocides, amide-based non-oxidative biocides and imide-based non-oxidative biocides, halogenated non-oxidative biocides, sulfur-containing non-oxidative biocides, quaternary phosphonium salt-containing non-oxidative biocides, ammonium salt-containing non-oxidative biocides and any combination thereof.

Aldehyde containing biocides may be linear, branched or aromatic. Examples of aldehyde-based biocide include, but are not limited to, formaldehyde, glutaraldehyde and acrolein.

Examples of halogenated biocides include, but are not limited to, bronopol, terbutylazine (TBZ), and halocyanoacetamides such as 1,2-dibromo-2,4-dicyanobutane (dibromodicyanobutane DBDCB), 2-bromo-2-cyano-acetamide, 2,2-dibromo-2-cyanoacetamide, 2-bromo-2-chloro-2-cyanoacetamide and 2-2-dibromo-3-nitrilopropionamide (DBNPA).

Exemplary sulfur-containing non-oxidative biocides include, but are not limited to, isothiazolone, thiocarbamates, thiocyanomethylbenzothiazole, copper sulfate and metronidazole.

Exemplary quaternary phosphonium salt-containing non-oxidative biocides include, but are not limited to, tetrakis (hydroxymethyl)phosphonium sulfate (THPS).

Preferably, the non-oxidative biocide is a halogenated non-oxidative biocide and more preferably it is a halocyanoacetamide, as detailed hereinabove and further as described, for example, in U.S. Pat. No. 3,928,575, which is incorporated by reference as if fully set forth herein.

According to the presently most preferred embodiments of the present invention, the non-oxidative biocide is DBNPA. DBNPA can be utilized as a single non-oxidative biocide or in combination with one or more additional non-oxidative biocides, as described herein.

The non-oxidative biocide(s) utilized in each of the formulations described herein can be selected upon the desired application of the formulation, namely, the most suitable agent for killing a target microorganism can be utilized.

The term "inorganic halide salt" refers to a salt of an inorganic element or moiety and one or more halides, whereby the number of halides depends on the valency of the inorganic element or moiety.

The term "halide" describes an anion of a halogen and can be fluoride, chloride, bromide or iodide. Preferably, the inorganic halide salt is an inorganic bromide salt, an inorganic chloride salt or a combination thereof.

As detailed in the background hereinabove, bromine-based oxidative agents are considered highly suitable for the treatment of industrial water, since at high pH levels, associated with industrial water, the hypobromous acid is a highly efficient biocide, is less affected by the presence of amines, and has a low volatility. Thus, according to preferred embodiments of the present invention, the inorganic halide salt is an inorganic bromide salt.

Exemplary inorganic bromide salts include, but are not limited to, sodium bromide, magnesium bromide, calcium bromide, lithium bromide, ammonium bromide and potassium bromide. According to the presently most preferred embodiment of the present invention, the inorganic halide salt is sodium bromide.

Thus, further according to the presently most preferred embodiments described herein, an aqueous suspension formulation, according to this aspect of the present invention, comprises DBNPA and a concentrated solution of sodium bromide.

As used herein, the phrase "concentrated aqueous solution" with respect to inorganic halide salt describes an aqueous solution in which the concentration of the halide salt is preferably higher than 5 weight percents, more preferably higher than 20 weight percents, and more preferably higher than 30 weight percents, and can be, for example 10 weight percents, 20 weight percents, 30 weight percents, 40 weight percents, and even 50 weight percents and 60 weight percents and higher, including any numeral from 10 to 60 and higher, depending on the saturation level of a particular salt.

Preferably, the concentrated inorganic halide salt is a saturated, or almost saturated, aqueous solution of the salt, also known and referred to herein as brine. Without being bound to any particular theory, it is suggested that the brine solution has a stabilizing yet dispersing effect on the formulation, and contributes to the high stability of the prepared suspensions, and to the desirable rheological properties thereof.

As can be seen in comparative experiments shown below (see for example, Examples 11 and 14), when water was used instead of brine, a more viscous suspension was obtained, rendering it difficult to pour and un-pumpable by a peristaltic pump.

A brine is achieved at different concentrations for different salts, depending on various aspects, such as the solubility of the salt, the temperature, the pH etc.

Typically, as is known in the art, when a mixture of a substance, and particularly a substance that has poor solubility in aqueous solutions, and a saturated aqueous solution of a salt is formed, an effect of salting out is observed, namely, the substance is separated from the aqueous solution and no uniform suspension is obtained. In the case of the present embodiments, stable and uniform suspensions of non-oxidative biocides are obtained and no salting out effect is observed.

As detailed in the background section hereinabove, halides may react with oxidizing agents to produce active halogens as strong oxidizing agents (oxidative biocides).

Thus, according to a preferred embodiment of the present invention, the halide salt is capable of producing an active halogen, as defined hereinabove, upon activation by an oxidizer.

Since, as explained in detail hereinabove, the hypobromous acid is a highly efficient biocide, preferably, the active halogen is active bromine.

As shown in scheme 2 hereinabove, a halide, such as bromide, can react with an oxidant such as hypochlorite, so as to generate the active hypobromous acid. This hypobromous acid generates an active bromine within the aquatic environment, which acts as an active oxidative biocide.

As used herein, the term "oxidizer" describes a substance that induces a change in an oxidizing state of another substance, by way of elevating the oxidizing state (reducing the number of electrons) of the other substance.

Preferably, the oxidizer may be any one or more of known oxidative biocides, such as, but not limited to a halogen oxidizer, a halogen carrier and a non halogen oxidizer.

Examples of halogen oxidizers include, but are not limited to chlorine, bromine, hypochlorite salts, hypochlorous acid, hypobromite salts and hypobromous acid.

Examples of halogen carriers, such as chlorine or bromine carriers, include, but are not limited to, halogenated hydantoins and halogenated isocyanurates.

Examples of non halogen oxidizers include but are not limited to, peroxides (such as hydrogen peroxide) and per sulfates (such as oxone).

According to a preferred embodiment of the present invention, the active halogen is prepared in situ, as defined hereinbelow, upon contacting the formulation described herein with an oxidizer, as described herein.

Further preferably, the combined system of a non-oxidative biocide, such as DBNPA, and an active halogen produced from a concentrated aqueous solution of a halide salt, act in synergy. As demonstrated in the Examples section that follows, it has been shown that the biocidal activity of a DBNPA/NaBr aqueous suspension, in the presence of an oxidizer, is higher than that of DBNPA and NaBr, when each is used alone, and is further higher that the sum of the activities exerted by each of these agents alone. Moreover, a synergistic biocidal activity was demonstrated when a system of microbial beads, simulating of a biofilm, was used. Treatment of such a system is very difficult and hence demonstration of a synergistic effect in such a system is particularly indicative.

Without being bound to any particular theory, it is suggested that utilizing the combined formulation of an oxidative and non-oxidative biocides presented herein involves a halide generating cycle, in which, in addition to the initial halide salt within the formulation, additional halide is continuously generated as a result of both DBNPA decomposition and hypobromous acid reaction.

Thus, according to another aspect of the present invention, there is provided a formulation which comprises at least one non-oxidative biocide, as described herein, a source of an in situ produced active halogen and an aqueous solvent. Such a formulation is preferably being in a form of a suspension.

As used herein, the phrase "a source of an in situ produced active halogen" describes a substance that is capable of producing an active halogen in situ, namely, via a reaction that occurs between an agent within the formulation and an agent in the treated medium (as opposed to an addition of an active halogen from an external source to the formulation). Preferably, such a substance reacts with an oxidizer that is contacted with the formulation, to thereby produce the active halogen. The in situ formed active halogen, serving as an oxidative biocide, acts together with the non-oxidative biocide, preferably in synergy, as detailed hereinabove.

Each of the formulations described herein are desirably characterized as capable of comprising the non-oxidative biocide and the halide salt, as described herein, in relatively large amounts, which provide for enhanced biocidal activity exerted thereby.

Thus, in preferred embodiments, an amount of a non-oxidative biocide together with an inorganic halide salt is greater than 30 weight percents of the total weight of the formulation, preferably greater than 50 weight percents and can therefore be, for example, 32 weight percents, 33 weight percents, 34 weight percents, 35 weight percents, 36 weight percents, 37 weight percents, 38 weight percents, 39 weight percents, 40 weight percents, 41 weight percents, 42 weight percents, 43 weight percents, 44 weight percents, 45 weight percents, 46 weight percents, 47 weight percents, 48 weight percents, 49 weight percents, 50 weight percents and even higher, for example, 51 weight percents, 52 weight percents, 53 weight percents, 54 weight percents, 55 weight percents, 56 weight percents, 57 weight percents, 58 weight percents, 59 weight percents, 60 weight percents, 60 weight percents, 61 weight percents, 61 weight percents, 63 weight percents, 64 weight percents, 65 weight percents, 66 weight percents, 67 weight percents, 68 weight percents, 69 weight percents, 70 weight percents, and up to 80 weight percents of the total weight of the formulation.

Further according to preferred embodiments of this aspect of the present invention, the formulation described herein contains a non-oxidative biocide in an amount that ranges from 3 weight percents to 70 weight percents, and preferably in an amount higher than 20 weight percents of the total weight of the formulation, and hence in an amount of, for example, 21 weight percents, 22 weight percents, 23 weight percents, 24 weight percents, 25 weight percents, 26 weight percents, 27 weight percents, 28 weight percents, 29 weight percents, 30 weight percents, 31 weight percents, 32 weight percents, 33 weight percents, 34 weight percents, 35 weight percents, 36 weight percents, 37 weight percents, 38 weight percents, 39 weight percents, 40 weight percents, 41 weight percents, 42 weight percents, 43 weight percents, 44 weight percents, 45 weight percents, 46 weight percents, 47 weight percents, 48 weight percents, 49 weight percents, 50 weight percents, 51 weight percents, 52 weight percents, 53 weight percents, 54 weight percents, 55 weight percents, 56 weight percents, 57 weight percents, 58 weight percents, 59 weight percents, 60 weight percents, and even higher, up to 65 weight percents, 66 weight percents, 67 weight percents, 68 weight percents, 69 weight percents, and even 70 weight percents of the total weight of the formulation.

While, as discussed hereinabove, currently available formulations of non-oxidative agents such as DBNPA are limited to relatively low concentrations of the biocide, it has now been found that stable formulations, containing much higher concentration of the biocide can be obtained.

As discussed hereinabove, the aqueous suspension formulations described herein, in addition to exhibiting an exceptional biocidal activity, are surprisingly and desirably characterized by other properties such as high stability and suitable viscosity.

As demonstrated in the Examples section that follows, these formulations were stable for prolonged time periods, reaching several weeks.

Thus, according to a preferred embodiment of the present invention, the aqueous suspension formulations described herein are stable for a time period of at least 7 days, preferably at least 10 days, when kept at ambient temperature (see, Examples 1, 2, 7, 8, 9, 12, 15 and 16).

The term "ambient temperature" refers to room temperature conditions, and is generally a temperature between about 18° C. and about 35° C.

Further, the aqueous suspension formulations described herein are preferably stable for a time period of at least 7 days when kept at 50° C. (see, Example 2).

As further discussed hereinabove, industrial suspensions are required to show a high viscosity at low shear rate, so as to avoid settling of the solid; and to show a low viscosity at higher shear rate, so as to permit flow and pumping of the suspension.

As demonstrated in Table 1 in the Examples section that follows, the aqueous suspension formulations presented herein exhibited high shear rates at low speeds (for example, 3 or 6 rpm), while exhibiting low shear rates at higher speeds (100, 200, 300 and 600 rpm).

According to preferred embodiments of this aspect of the present invention, the aqueous suspensions described herein are therefore advantageously characterized by such a viscosity, that at low speeds, namely at a speed smaller than 100 rpm, the shear rate is higher than 300 Pascals (Pa). According to some of the presently most preferred embodiments, at such speeds, the shear rate is higher than 700 Pa, higher than 1200 Pa and even higher than 2000 Pa.

According to preferred embodiments of this aspect of the present invention, the aqueous suspensions described herein are also advantageously characterized by such a viscosity, that at high speeds, namely at speeds equal to or higher than 100 rpm, the shear rate is lower than 300 Pa. According to some of the presently most preferred embodiments, at such speeds, the shear rate is lower than 100 Pa and even lower than 50 Pa.

The rheological behavior of suspensions is typically dependant, inter alia, on the solid particles' size.

Thus, according to a preferred embodiment of the present invention, the average particle size of the non-oxidative biocide is less than 200 microns. Preferably, the average particle size of the non-oxidative biocide is less than 100 microns, more preferably less than 50 microns, and more preferably less than 20 microns. For example, DBNPA suspensions have been prepared, wherein the average particle size of the DBNPA was 57 microns (Example 14), 20 microns (Example 11) and 29 microns (Example 10). These suspensions exhibited excellent stability and good rheological properties.

The particle size may further be characterized, in addition or in place of the average particle size, by the d50 or d98 values thereof, meaning the size under which 50% of the particles reside (d50), or the size under which 98% of the particles reside.

Thus, according to a preferred embodiment of the present invention, the d50 of the non-oxidative biocide particles size is less than 50 microns, preferably less than 10 microns. Yet according to another preferred embodiment of the present invention, the d98 of the non-oxidative biocide particles size is less than 100 microns, preferably less than 50 microns.

The aqueous suspension formulations described herein may further comprise a suspending agent. Preferably, the suspending agent is a water-soluble suspending agent. Exemplary suspending agent include, but are not limited to, xanthan gum, sodium carboxymethylcellulose, polyacrylic acid, tragacanth, polymethyl vinyl ether/maleric anhydride copolymer, polyethylene oxide, methylcellulose, karya gum, methylethylcellulose, soluble starch, geletan, pectin, polyvinyl alcohol, polyhydroxymethacrylate, hydroxypropyl cellulose, carbomers, chitin, gum acacia, and mixtures thereof.

Foaming agents may also be used to stabilize the suspension in a form of "foam", as shown, for example, in Example 1 hereinbelow. A representative example of a suitable foaming agent is linear alkyl benzene sulfonic acid (LABS).

The amount of the suspending agent and/or foaming agent can range from 0.01 weight percent to 5 weight percents of the total weight of the formulation.

As shown, however, in the Examples section that follows, due to the stability of the suspensions, relatively low amount of these agents can be utilized. Thus, preferably, the amount of the suspending agent and/or foaming agent is lower than 2 weight percents, and more preferably ranges from 0.3 weight percent to 1.1 weight percents of the total weight of the formulation.

As demonstrated in the Examples section that follows, treating a cooling water tower with a combination of sodium hypochlorite (10%) oxidizer and a 55% milled DBNPA formulations, containing a NaBr 40% brine, resulted in a substantial reduction of the microbial count from more than $10^5$ CFU/ml to less than $10^3$ CFU/ml, indicating a high biocidal activity. Thus, any of the formulations described herein may be used in water disinfection, and may suitably be identified as such.

The aqueous suspension formulations described herein are thus highly suitable to disinfect water, having the following advantages:
- the formulations are effective biocides;
- the formulations are solvent-free, which is an environmental, economical and biocidal advantage, as detailed hereinabove;
- the aqueous suspension formulations are both stable and pourable, thus suitable for the treatment of water bodies;
- the formulations are easy to control and add to water systems, being aqueous suspensions and not solid formulations;
- the formulations can contain high concentrations of biocides, and are thus suitable to use in the treatment of heavily polluted or infected water systems with significant logistics and handling advantages;
- the formulations exhibit a synergistic effect by the combination of both a non-oxidative biocide and a concentrated aqueous halide salt, which keeps generating fresh halides in situ, in the presence of common oxidizers.

As further demonstrated in the Examples section that follows, while maintaining the methodology of using a combination of a non-oxidative biocide and a substance that can act as a source of an in situ produced active halogen, the present inventors have successfully practiced liquid formulations that comprise such a combination. More specifically, the present inventors have prepared stable liquid formulations of a non-oxidative biocide such as DBNPA, in a relatively high concentration, and inorganic halide salts, which further include an organic solvent, in a relatively low amount. By using a high concentration of the non-oxidative biocide, lower amounts of the formulation are required during a water treatment process, thus circumventing the limitations associated with excessive amounts of organic solvents. Obviously, by using lower amounts of an organic solvent, the limitations associated with excessive amounts of organic solvents are also circumvented.

As described in detail in the background hereinabove, presently known non-oxidative biocidal liquid formulations, such as DBNPA liquid formulations contain at least 45% by weight of a glycol, such as PEG, in order to achieve stability, and the amount of DBNPA rarely exceeded 25% (see, for example, U.S. Pat. Nos. 3,689,660, 4,163,796, 4,163,797, 4,163,795 and 4,232,041 and DE 2,854,078, supra).

Thus, according to another aspect of the present invention there is provided a liquid formulation which comprises at least one non-oxidative biocide, as described herein, a concentrated aqueous solution of an inorganic halide salt, as described herein, and a polyalkylene glycol. Preferably, the polyalkyleneglycol has a molecular weight higher than 100 Daltons (Da), more preferably higher than 200 Da, as detailed hereinbelow.

Further preferably, the amount of the non-oxidative biocide in such a formulation is 20 weight percents of the total weight of the formulation, and more preferably is higher than 20 weight percents of the total weight of the formulation, and can be, for example, 25 weight percents, 30 weight percents, 35 weight percents, 40 weight percents, 45 weight percents, 50 weight percents, 55 weight percents, 60 weight percents and even higher, including any other numeral between 20 and 70 weight percents of the total weight of the formulation As used herein the term "polyalkylene glycol", encompasses liquid and solid polymers of the general formula HO—[(CH$_2$)m-O-]nCH$_2$OH, where m is an integer from 2 to 6 and n is greater than or equal to 4.

Preferably the polyalkylene glycol is a polyethylene glycol, also referred to herein as its abbreviation PEG.

Exemplary polyethylene glycols that are suitable for use in this context of the present invention include, but are not limited to, polyethylene glycols having a molecular weight greater in the range of 100 to 2,000 (Da) such as PEG 100, having an average molecular weight of about 100 Da, PEG 200, having an average molecular weight of about 200 Da, PEG 300, having an average molecular weight of about 300 Da, PEG 400, having an average molecular weight of about 400 Da, PEG 600, having an average molecular weight of about 600 Da, PEG 1000, having an average molecular weight of about 1000 Da, and up to PEG 2000, having an average molecular weight of about 2000 Da. Preferably, the polyethylene glycol has an average molecular weight in the range of from 200 Da to 400 Da.

Surprisingly, it has now been found that a lower amount of PEG can be used while maintaining the stability of the formulation. For example, it has been found that a liquid formulation containing 20 weight percents DBNPA, 32 weight percents PEG 400, water and NaBr, is stable (see, Example 4 hereinbelow), while the same formulation excluding the sodium bromide resulted in a precipitation of solid DBNPA at the bottom of the flask (see Example 5 hereinbelow).

Thus, in preferred embodiments, an amount of the polyethylene glycol is lower than 50 weight percents of the total weight of the formulation, preferably lower than 45 weight percents, more preferably lower than 40 weight percents, more preferably lower than 35 weight percents, and more preferably lower than 30 weight percents.

Further according to preferred embodiments, the concentration of the inorganic halide salt (e.g., sodium bromide) utilized in such formulations ranges from 10 weight percents to 40 weight percents.

Preferably, the formulations according to these embodiments of the present invention do not include hypobromous acid or any other oxidizing agent. Further preferably, these formulations are devoid of HBr.

As discussed hereinabove, the present inventors have shown that highly active biocidal formulations, in various forms, are obtained by utilizing a non-oxidative biocide and a substance that can produce an active halogen in situ (e.g., an inorganic halide salt), as defined herein.

Thus, according to another aspect of the invention, there is provided a method of water disinfestation, which is effected by contacting the water with at least one non-oxidative biocide and an in situ produced active halogen.

The contacting may be performed intermittently or continuously.

The method may further be effected by contacting the water with an oxidizer, as detailed hereinabove.

Further according to the present invention there is provided a method of treating water, which is effected by contacting the water with any of the formulations described herein.

In a typical process, the water source is treated by a continuous or batch wise addition of an oxidizer (e.g., 10% sodium hypochlorite solution), which is replaced occasionally by a formulation containing a non-oxidative biocide, according to the present embodiments, whereby replacing the two treatment solutions by one another can be performed repetitively. Thus, water is treated by an oxidizer solution, then by a non-oxidative biocide formulation, then by an oxidizer solution, and so on. The time interval between switching the treatment solution and the time during which each treatment solution is applied are determined according to the treated system.

The formulations and methods described herein can be used in many water treatment applications. Exemplary applications include treatment of drinking water, sewage water, process water systems, such as in papermaking or in industrial cooling water systems, washing water, heavy oil sludges, cutting oils, lignin-containing waste liquors, textile oils and other liquid targets in order to kill, prevent or inhibit the growth of microorganisms as described herein.

The formulations described herein are typically prepared by mixing the at least one non-oxidative biocide and the concentrated aqueous solution of an inorganic halide salt, and may optionally include the mixing of additional ingredients, as described in detail hereinabove.

In cases where the formulations are aqueous suspension formulations, preferably, the preparation process optionally further comprises milling the DBNPA in the mixture.

In cases where the formulations are liquid formulations, the preparation process preferably include mixing and dissolving of the various components.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Analytical Methods

DBNPA and NaBr brine solution were obtained from ICL Industrial Products.

Linear alkyl benzene sulfonic acid (LABS) was obtained from Zohar Dahlia.

Xanthan gum was obtained from SIGMA. Xanthan gum concentrations indicated below are relative to the brine weight, unless otherwise specified.

Polyethylene glycols (PEG 200 and PEG 400) were obtained from Merck (Germany).

Sodium hypochlorite (10%) was obtained from F&C LTD.

Zirconia grinding balls were obtained from IMI ceramics laboratory.

Isothiazolinon-based non-oxidant biocide LABUZID 197 was obtained from BK Giulini.

Homogenization was performed using an Ultra-Turrax T25 (IKA Germany) dispersing system equipped with a S25-25 GM dispersing element.

The particle size was determined by laser Diffractometry. The viscosity was measured using a Fann viscometer.

Example 1

A Homogenized Suspension of 40% DBNPA, 40% NaBr Brine and 1% Linear Alkyl Benzene Sulfonic Acid (LABS)

A NaBr aqueous solution (40% (brine), 295 grams) was mixed with a linear alkyl benzene sulfonic acid (LABS) solution (1%, 5 grams) and with 2-2-dibromo-3-nitrilopropionamide (DBNPA) (200 grams) in a 500 ml beaker. The mixture was homogenized in a dispersing system at 24,000 rpm for 2 minutes. A triphasic "foam" (suspension with air inside) was obtained, having a density of about 1.4 kg/liter. The mixture was stored for one week in a 500 ml graduated cylinder. No settling of the solid was observed and the suspension remained homogeneous.

Example 2

A Homogenized Suspension of 55% DBNPA, 40% NaBr Brine and 0.55% Xanthan Gum

A NaBr aqueous solution (40% (brine), 270 grams) was mixed with xanthan gum (1.5 grams) and DBNPA (330 grams) in a 500 ml beaker. The mixture was homogenized in a dispersing system, at 10,000 rpm for 2 minutes and a suspension was obtained. The average particle size of the DBNPA in the suspension was about 180 µm. The density of the suspension was 1.7 Kg/liter. The suspension was easily poured and pumped using a peristaltic pump.

The suspension was stored for one month at ambient temperature in a 500 ml graduated cylinder, and another batch was stored for one week at 50° C. The density of the upper and lower part of the suspension was in the range of 1.68-1.70 Kg/liter in both cases, indicating there was no settling of the DBNPA.

Example 3

A Homogenized Suspension of 66% DBNPA, 40% NaBr Brine, and 0.74% Xanthan Gum

A NaBr aqueous solution (40% (brine), 403 grams) was mixed with xanthan gum (3 grams) and DBNPA (817 grams) in a 800 ml beaker. The mixture was homogenized in a dispersing system, with S25-25 GM dispersing element at 24,000 rpm for 2 minutes, to thereby obtain a suspension. The mixture was easily poured and pumped with a peristaltic pump.

Example 4

A Solution of 20% DBNPA, PEG 400, Water and Solid NaBr

DBNPA (40 grams) was mixed with PEG 400 (64 grams, 32%) and water (72 grams) at 50° C. NaBr (24 grams) was then added and the obtained solution was frozen and stored overnight at −15° C. After thawing, no solid precipitates were observed in the mixture.

Example 5

A Solution of 20% DBNPA in a PEG 400 and Water Mixture

As a comparative example, a solution as described in Example 4 was prepared, with the exclusion of NaBr.

DBNPA (40 grams) was mixed with PEG 400 (82 grams) and water (78 grams) at 50° C., and the obtained solution was frozen and stored overnight at −15° C. After thawing, solid precipitate of DBNPA appeared at the bottom of the solution.

Example 6

A Solution of 20% DBNPA in a PEG 200 and Water Mixture

As another comparative example, a solution as described in Example 5 was prepared, using PEG 200 instead of PEG 400.

DBNPA (40 grams) was mixed with PEG 200 (96 grams) and water (64 grams) at 50° C., and the obtained solution was frozen and stored overnight at −15° C. After thawing, solid precipitate of DBNPA appeared at the bottom of the solution.

Example 7

A Homogenized Suspension of 20% DBNPA, 40% NaBr Brine and 0.6% Xanthan Gum

A NaBr aqueous solution (40% (brine), 480 grams) was mixed with xanthan gum (3.0 grams) and DBNPA (120 grams) in a 1000 ml beaker. The mixture was homogenized in a dispersing system at 10,000 rpm for 2 minutes, to thereby obtain a suspension. The mixture was easily poured from the beaker. The suspension was stored for 10 days at ambient temperature in a 500 liter graduated cylinder with no decantation (settling) being observed. The suspension was easily pumped with a peristaltic pump. The mixture was stored for one week at ambient temperature with no decantation being observed. After storage, the DBNPA concentration in the upper and lower 70 ml portions of the suspension was 20%, indicating no settling of the DBNPA.

Example 8

A Homogenized Suspension of 55% DBNPA, 40% NaBr Brine and 1.1% Xanthan Gum

A NaBr aqueous solution (40% (brine), 270 grams) was mixed with xanthan gum (3.0 grams) and DBNPA (330 grams) in a 1000 ml beaker. The mixture was homogenized in a dispersing system at 10,000 rpm for 2 minutes, to thereby obtain a suspension. The mixture was easily poured from the beaker and pumped with a peristaltic pump. The suspension was stored for one week at 50° C. in a 500 liter graduated cylinder with no decantation being observed.

Example 9

A Homogenized Suspension of 20% DBNPA, 10% NaBr Brine and 0.6% Xanthan Gum

A NaBr aqueous solution (10% (brine), 480 grams) was mixed with xanthan gum (3.0 grams) and DBNPA (120 grams) in a 1000 ml beaker. The mixture was homogenized in a dispersing system at 10,000 rpm for 2 minutes, to thereby obtain a suspension. The mixture was easily poured from the beaker. The suspension was stored for 10 days at ambient temperature in a 500 liter graduated cylinder with no decantation being observed. The suspension was easily pumped with a peristaltic pump.

Example 10

A Homogenized Milled Suspension of 55% DBNPA, 40% NaBr Brine and 0.5% Xanthan Gum A NaBr aqueous solution (40% (brine), 540 grams) was mixed with xanthan gum (2.7 grams) and DBNPA (660 grams) in a 2 liter plastic bottle of 12 cm diameter filled with 2.9 kg of 6 mm diameter zirconia grinding balls. The mixture was homogenized in a dispersing system at 10,000 rpm for 2 minutes, to thereby obtain a suspension. The mixture was rolled for one hour at 60 rpm, and the obtained suspension was separated from the balls. The particle size distribution was determined as d50 of 29 µm and d98 of 76 µm. A 5 ml portion of the suspension was put in an agitated beaker containing 1 liter of water, determining the total dissolution time of the particles to be 30 seconds. The mixture was easily poured and pumped using a peristaltic pump. No settling of the solid was observed and the suspension remained homogeneous.

Example 11

A Milled Suspension of 55% DBNPA, Water, and 0.5% Xanthan Gum (Relative to Water)

As a comparative example, a milled suspension was prepared as described in Example 10 above, with the exclusion of NaBr. Thus, water (540 grams) were mixed with xanthan gum (2.7 grams) and DBNPA (660 grams) in a 2 liter plastic bottle of 12 cm diameter, filled with 2.9 kg of 6 mm diameter zirconia grinding balls. The mixture was rolled for one hour at 75 rpm and the obtained suspension was then separated from the balls. The particle size distribution was determined as d50 of 5.5 µm and d98 of 40 µm. The suspension was viscous, difficult to pour and was not pumpable by a peristaltic pump.

Example 12

A Homogenized Milled Suspension of 20% DBNPA, 40% NaBr Brine and 0.3% Xanthan Gum A NaBr aqueous solution (40% (brine), 480 grams) was mixed with xanthan gum (1.5 grams) and DBNPA (120 grams) in a 1000 ml beaker. The mixture was homogenized in a dispersing system at 10,000 rpm for 2 minutes, and placed in a 1 liter plastic bottle of 12 cm diameter filled with 1.4 kg of 6 mm diameter zirconia grinding balls. The mixture was rolled for 4 hours at 100 rpm, and the obtained suspension was separated from the balls. The suspension was stored for 10 days at ambient temperature in a 500 L graduated cylinder and no decantation has been observed.

Example 13

A Homogenized Milled Suspension of 55% DBNPA in Water and 0.5% Xanthan Gum

Water (540 grams) were mixed with a xanthan gum (2.7 grams) and DBNPA (660 grams) in a 2 liter plastic bottle of 12 cm diameter filled with 2.9 kg of 6 mm diameter zirconia grinding balls. The mixture was rolled for 1 hour at 75 rpm, and the obtained suspension was hardly separated from the balls. The mixture was difficult to pour and was too viscous to be pumped. The particle size distribution was determined to be: d50 of 5.5 µm and d98 of 40 µm. These findings indicate an important role for an inorganic salt in forming a stable formulation that has desirable rheological properties.

Example 14

A Homogenized Milled Suspension of 55% DBNPA in Water and No Xanthan Gum

Water (540 grams) were mixed with DBNPA (660 grams) in a 2 liter plastic bottle of 12 cm diameter filled with 2.9 kg of 6 mm diameter zirconia grinding balls. The mixture was rolled for 1 hour at 75 rpm, and the obtained suspension was hardly separated from the balls. The average particle size of the DBNPA in the suspension was of 57 µm. The mixture was difficult to pour and was too viscous to be pumped. The particle size distribution was determined to be: d50 of 57 µm and d98 of 148 µm. These findings further support the important role of an inorganic salt in forming a stable formulation that has desirable rheological properties.

Example 15

A Homogenized Suspension of 55% DBNPA, 60% LiBr Brine and 0.45% Xanthan Gum A LiBr aqueous solution (60% (brine), 270 grams) was mixed with a xanthan gum (1.5 grams) and DBNPA (330 grams) in a 500 ml beaker. The mixture was homogenized in a dispersing system at 10,000 rpm for 2 minutes, to thereby obtain a suspension. The mixture was easily poured from the beaker and pumped with a peristaltic pump. The suspension was stored for one week at ambient temperature and the solids level was determined to be 87% of the suspension volume. The material could be easily pumped by a peristaltic pump. These findings show that various inorganic halide salts can be utilized in the context of the present embodiments.

Example 16

A Homogenized Suspension of 55% DBNPA, 40% NH4Br Brine and 0.45% Xanthan Gum A NH$_4$Br aqueous solution (40% (brine), 270 grams) was mixed with a xanthan gum (1.5 grams) and DBNPA (330 grams) in a 500 ml beaker. The mixture was homogenized in a dispersing system at 10,000 rpm for 2 minutes, to thereby obtain a suspension. The mixture was easily poured from the beaker and pumped with a peristaltic pump. The suspension was stored for one week at ambient temperature and the solids level was determined to be 97% of the suspension volume.

The material could be easily pumped by a peristaltic pump. These findings further support the indication that various inorganic halide salts can be utilized in the context of the present embodiments.

Example 17

Rheological Measurements of DBNPA Suspensions

The viscosity was measured for the suspensions prepared according to the processes described in Examples 7, 9, 10, 12, 13, 15 and 16. The results are presented in Table 1 below.

TABLE 1

| Example No. | % DBNPA | Salt | % Salt | % xanthan gum | Shear stress (Pa) at different speeds (rpm) | | | | | |
|---|---|---|---|---|---|---|---|---|---|---|
| | | | | | 3 RPM | 6 RPM | 100 RPM | 200 RPM | 300 RPM | 600 RPM |
| 7 | 20 | NaBr | 40 | 0.6 | 2200 | 1200 | 140 | 87 | 68 | 43 |
| 9 | 20 | NaBr | 10 | 0.6 | 1500 | 750 | 87 | 56 | 44 | 29 |
| 10 | 55 (milled) | NaBr | 40 | 0.5 | — | — | 275 | 205 | 180 | 145 |
| 12 | 20 (milled) | NaBr | 40 | 0.3 | 700 | 350 | 54 | 38 | 31 | 22 |
| 13 | 55 (milled) | — (water) | | 0.5 | 2200 | 1250 | 245 | 195 | 160 | 115 |
| 15 | 55 | LiBr | 60 | 0.45 | 2100 | 1400 | 285 | 206 | 167 | 118 |
| 16 | 55 | NH$_4$Br | 40 | 0.45 | 2400 | 1300 | 195 | 115 | 95 | 62 |

Example 18

A Solution of 20% DBNPA, PEG 400 and Water

DBNPA (40 grams) was mixed with PEG 400 (82 grams) and water (78 grams) at 50° C., and the obtained solution was frozen and stored overnight at −15° C. After thawing there was no solid deposit at the bottom of the solution.

Example 19

A Solution of 20% DBNPA, PEG 400, Water and Solid NaBr

DBNPA (40 grams) was mixed with PEG 400 (64 grams) and water (72 grams) at 50° C. NaBr (24 grams) was then added and the obtained solution was frozen and stored overnight at −15° C. After thawing there was no solid deposit at the bottom of the solution.

Example 20

A Solution of 20% DBNPA in a PEG 200 and Water

DBNPA (40 grams) was mixed with PEG 200 (96 grams) and water (64 grams) at 50° C., and the obtained solution was frozen and stored overnight at −15° C. After thawing there was no solid precipitate.

Example 21

A Solution of 20% DBNPA Using PEG 200, Water and Solid NaBr

DBNPA (40 grams) was mixed with PEG 200 (76 grams) and water (60 grams) at 50° C. NaBr (24 grams) was then added and the obtained solution was frozen and stored overnight at −15° C. After thawing there was no solid deposit.

Example 22

Field Tests

A cooling tower of 1000 m$^3$ was treated by addition of sodium hypochlorite (10%) in a continuous mode at a rate of 60 liters per day, 24 hours per day. A typical solution of an isothiazolinon-based non-oxidant biocide was added, instead of the sodium hypochlorite, twice a week. The microbial count was of more than 10$^5$ Colony Forming Units (CFU)/ml. Fouling related local corrosion was observed. Due to the high halogen demand the free halogen content was lower than 0.1 ppm already one hour after the addition of the sodium hypochlorite. The pH of the water was in the range 8-8.5.

The addition of the isothiazolinon-based non-oxidant biocide was stopped and sodium hypochlorite (50 liters) was added to the cooling tower at a constant flow-rate 19 hours per day. Two hours after the sodium hypochlorite addition was ceased, the suspension prepared as described in Example 10 was added (7 kg) once every two days. The sodium hypochlorite addition was renewed three hours later. As a result of this treatment, the bacterial count was reduced to lower than 10$^3$ CFU/ml. After a week of treatment, the free halogen content in the cooling water was of 0.5 ppm of bromine (expressed as chlorine). No fouling-related local corrosion was observed in the corrosion samples.

Example 23

Experiments on Simulated Biofilm Showing a Synergistic Effect

Experimental Method:

The experiments were conducted based on a biofilm simulation system developed by the Biofilm Institute in Bozeman Mont. (Grobe et al., J. of Industrial Microbiology & Biotechnology, vol. 29 pp. 10-15), which allows quantifying the resistance of a biofilm to biocides.

Biofilm Stimulation:

The biofilm simulation was created by entrapping bacteria in alginate gel beads. A plate of R2A agar was streaked with *Pseudomonas aeruginosa* (ATCC 15442) and incubated at 35° C. overnight. A phosphate buffer (pH 7.2) was used to scrap off the bacteria from the agar plate and create a suspension. The bacteria suspension was mixed with a 4% sodium alginate solution at a ratio of 1:1, to obtain an alginate and bacteria slurry containing a 2% alginate solution.

The alginate and bacterial slurry was placed in a 50 ml syringe equipped with a 22 gauge needle, connected to a compressed air tank, which allowed the syringe to be pressurized. A stream of small drops of the alginate and bacterial slurry was forced out and dropped into a stirred solution of 50 mM $CaCl_2$. The $Ca^{+2}$ cross-linked the alginate, and semisolid beads with entrapped bacterial cells were formed. The bead were stirred in the $CaCl_2$ solution for about 20 minutes, then rinsed in a dilute 5 mM $CaCl_2$ solution.

Several flasks containing 100 beads each were incubated overnight at 35° C. on a rotating shaker in a buffer solution (at desired pH), and a solution of 5 mM $CaCl_2$ was added to each beaker to maintain the beads structure. The beads diameter was about 2 mm.

Measurements of Biocidal Activity:

The buffer suspension, containing the 5 mM $CaCl_2$ solution, was first decanted and replaced by a 100 ml of the tested solution at the desired concentration.

A DBNPA/NaBr suspension, combining 58% DBNPA, 17% NaBr salt and 25% $H_2O$, was applied in combination with a sodium hypochlorite (NaOCl) solution in two addition modes (routes): (a) addition of the sodium hypochlorite to the test system and following 15 minutes addition of the DBNPA/NaBr suspension; and (b) addition of the DBNPA/NaBr suspension and following 15 minutes addition of sodium hypochlorite. NaOCl was added in an amount calculated so as to achieve a 1 ppm activated NaBr in the suspension.

At different time intervals, 10 beads were removed and placed in a 5 grams/liter sodium thiosulfate solution containing 50 mM sodium citrate. The sodium citrate dissolves the alginate gel and releases the bacteria into the solution.

The neutralizer-citrate solution was placed in a refrigerator for 2 hours, and was thereafter diluted and plated on R2A agar plates using pour plate technique. The plates were incubated at 35° C. for 24-48 hours and than tested for bacteria counted.

The results were analyzed upon testing the neutralizer efficacy and toxicity and were compared to the control samples.

Experimental Results:

The potential synergistic effect between DBNPA, as a non-oxidative biocide, and activated NaBr, as an oxidative biocide, was tested.

Synergism refers, as further defined hereinabove, to the phenomenon in which two (or more) materials acting together create an effect greater than that predicted by knowing only the separate effects of each individual material.

The results are presented in FIG. 1 and clearly show that (i) no biocidal effect was observed in the presence of 1 ppm activated NaBr; (ii) exposure of the beads to 2.5 ppm DBNPA, resulted in 3 log reduction (as compared to control) after 30 minutes contact time. The same results were obtained for the activated NaBr/DBNPA suspension, added following the addition of the oxidative agent (route (a) hereinabove). Adding a suspension of NaBr/DBNPA and then sodium hypochlorite, via route (b) hereinabove, resulted in complete kill after 30 minutes contact time, indicating a synergistic effect between the two components.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A formulation in the form of a suspension consisting essentially of solid particles of 2,2-dibromo-3-nitrilopropionamide (DBNPA) in a suspension-stabilizing amount of sodium bromide brine, the suspension remaining stable for at least 7 days when kept at 50° C. but in the absence of said suspension-stabilizing amount of sodium bromide brine, failing to remain stable for at least 7 days when kept at 50° C.

2. The formulation of claim 1, wherein said sodium bromide produces an active bromine upon activation by an oxidizer.

3. The formulation of claim 2, wherein said oxidizer is at least one member selected from the group consisting of chlorine, bromine, hypochlorite salt, hypochlorous acid, hypobromite salt, hypobromous acid a halogenated hydantoin, a halogenated isocyanurate, a peroxide and a persulfate.

4. The formulation of claim 1, further comprising at least one additional biocide.

5. The formulation of claim 1, wherein an amount of said DBNPA and said sodium bromide is greater than 30 weight percent of the total weight of the formulation.

6. The formulation of claim 1, wherein an amount of said DBNPA ranges from 3 weight percent and 70 weight percent of the total weight of the formulation.

7. The formulation of claim 6, wherein an amount of said DBNPA is greater than 20 weight percent of the total weight of the formulation.

8. The formulation of claim 1, wherein said DBNPA and said sodium bromide and/or active halogen formed thereby act in synergy.

9. The formulation of claim 1 which is substantially free of organic solvent.

10. The formulation of claim 1, further comprising a foaming agent.

11. The formulation of claim 1, further comprising a linear alkyl benzene sulfonic acid foaming agent.

12. The formulation of claim 1, wherein the sodium bromide brine contains from 5 weight percent up to its saturation level of sodium bromide.

13. The formulation of claim 1, wherein the sodium bromide brine contains sodium bromide in an amount which at or near its saturation level.

14. The formulation of claim 1, characterized by a shear rate higher than 300 Pa at a speed small than 100 rpm.

15. The formulation of claim 1, characterized by a shear rate lower than 300 Pa at a speed equal to or higher than 100 rpm.

16. The formulation of claim 1, wherein the average particle size of DBNPA in the suspension is less than 200 microns.

17. The formulation of claim 1, wherein the average particle size of DBNPA in the suspension is less than 10 microns.

18. The formulation of claim 1 further comprising a suspending agent.

19. The formulation of claim 1 further comprising at least one water-soluble suspending agent selected from the group consisting of xanthan gum, sodium carboxymethylcellulose, polyacrylic acid, tragacanth, polymethyl vinyl ether/maleric anhydride copolymer, polyethylene oxide, methylcellulose, karya gum, methylethylcellulose, soluble starch, geletan, pectin, polyvinyl alcohol, polyhydroxymethacrylate, hydroxypropyl cellulose, carbomers, chitin and gum acacia.

\* \* \* \* \*